(12) United States Patent
Zhang

(10) Patent No.: US 9,480,640 B2
(45) Date of Patent: Nov. 1, 2016

(54) NANO FREEZE DRY PROCESS OF PREPARATION OF HIGHLY BIOACTIVE AGENT AND ITS METHOD OF USE

(71) Applicant: Hongkai Zhang, Shanghai (CN)

(72) Inventor: Hongkai Zhang, Shanghai (CN)

( * ) Notice: Subject to any disclaimer, the term of this patent is extended or adjusted under 35 U.S.C. 154(b) by 262 days.

(21) Appl. No.: 14/495,280

(22) Filed: Sep. 24, 2014

(65) Prior Publication Data
US 2016/0081911 A1 Mar. 24, 2016

(51) Int. Cl.
*A61K 36/00* (2006.01)
*A61K 8/97* (2006.01)
*A61Q 19/08* (2006.01)

(52) U.S. Cl.
CPC .............. *A61K 8/97* (2013.01); *A61Q 19/08* (2013.01); *A61K 2800/413* (2013.01); *A61K 2800/84* (2013.01)

(58) Field of Classification Search
None
See application file for complete search history.

(56) References Cited

U.S. PATENT DOCUMENTS

2010/0136126 A1\* 6/2010 Lee et al. ...................... 424/497

\* cited by examiner

*Primary Examiner* — Qiuwen Mi
(74) *Attorney, Agent, or Firm* — Novoclaims Patent Services LLC; Mei Lin Wong

(57) ABSTRACT

A nano freeze dry process of preparation for a cosmetic composition having a bioactive agent for providing an anti-aging effect on a skin, comprising the steps of: placing the cosmetic composition having a bioactive agent into a capsule container; and nano freeze drying the cosmetic composition by: freezing the cosmetic composition in the capsule container at −170° C.; increasing the temperature to −85° C. and allowing sublimation under vacuum condition; then increasing the temperature to 35° C.; and vacuum drying to obtain a final product, wherein a volume of the cosmetic composition remains unchanged after the process, a water content of less than 5% is inside the final, at least 80% of bioactivity of the cosmetic composition is retained, and significant anti-aging effect is observed after a two-day treatment.

8 Claims, 3 Drawing Sheets

NANO FREEZE DRY PROCESS OF PREPARATION OF HIGHLY BIOACTIVE AGENT AND ITS METHOD OF USE

BACKGROUND OF THE PRESENT INVENTION

1. Field of Invention

The present invention relates to a process of preparation of bioactive agent, and more particularly to a process of preparation of bioactive agent which utilizes a freeze dry process to obtain a bioactive agent which is resized to nano-scale while retaining its original bioactivity. In particular, the bioactive agent is a cosmetic compositions for external use and is capable of being applied onto the skin of a user and instantaneous absorbed by the user through the skin with unexpected high rate of absorption and dispersion to produce a fast and significant beauty effect.

2. Description of Related Arts

Common cosmetic compositions, such as lotion, cream, serum or liquid spray, are usually applied onto the skin of a user and are absorbed through the skin of the user. However, the absorption rate or the ability of the cosmetic compositions to penetrate through the skin is not sufficiently high. In addition, some ingredients, especially bioactive ingredients, are not suitable for preparation into lotion, cream, serum, liquid spray or the like because of its poor penetration and absorption rate through the skin and/or the difficulties in preserving the bioactivity of the particular ingredient. In other words, convention method of preparation of cosmetic compositions fails to achieve a high penetration and absorption rate to the skin while is restrictive to particular kind of ingredients.

The contents of the conventional cosmetic compositions are very restrictive in a sense that highly bioactive agents such as bioactive natural raw materials are very hard to be contained or preserved in the cosmetic compositions without the loss of bioactivity of the natural raw materials. The use of preservatives is able to extend the product life or preserve the bioactivity of the product. However, the use of preservatives also imposes an adverse effect on the nature and purity of the product and hence affect the activity of the active ingredients of the cosmetic compositions.

Conventional cosmetic compositions usually has a short storage period due to its stability, its sensitivity to temperature changes and its loss of activity over time. In general, the effective period is about two years with acceptable level of preservatives. There does not exist any method to extend the effective period in view of the conventional technologies.

Conventionally, common cosmetic compositions are intended for external use. For example, cosmetic compositions, such as lotion, cream, serum or liquid spray, are applied onto the skin of a user and are absorbed through the skin of the user. However, some types of compositions has very poor penetration and absorption rate and is very ineffective or unpredictable when used externally onto the skin. In addition, through aging and undesirable environmental effect or stimulation such as prolonged exposure to sunlight, the ability of skin to response to the application of cosmetic compositions will be lowered. In other words, cosmetic compositions, which aim at nourishing, restoring, replenishing and refreshing the skin, will be challenged by the aging effect and the environmental effect because the ability of the skin to absorb or regenerate is very poor.

Accordingly, highly bioactive ingredients are very desirable for cosmetic compositions. For example, anti-wrinkle lotion for combatting the aging effect over time, will require a sufficient strength in order to nourish, restore, replenish and refresh the skin. Under aging skin conditions, the use of highly bioactive ingredients is very desirable but the conventional compositions are restricted by the conventional method of preparation and uses.

SUMMARY OF THE PRESENT INVENTION

In view of the above problems of convention method of preparation of cosmetic compositions, an object of the present invention is to provide a nano freeze dry process of preparation for cosmetic compositions primarily made of natural ingredients such that highly bioactive agents of the cosmetic compositions are retained and preserved for an unexpectedly long period of time without the need of the use of any preservatives while the particle size of the cosmetic compositions are broken down into nan-scale for facilitating instant absorption to the skin of a user.

Another object of the present invention is to provide a cosmetic composition being contained in a single-use vacuum capsule by a nano freeze dry process of preparation such that the cosmetic composition have a maximum effective period of 8 years and the bioactivity of the cosmetic composition is at least 80% of its original form within the effective period.

Another object of the present invention is to provide for cosmetic composition for providing anti-aging effect by a nano freeze dry process of preparation such that highly bioactive agents of the cosmetic compositions are retained and preserved for an unexpectedly long period of time without the need of the use of any preservatives while the particle size of the cosmetic compositions are broken down into nan-scale for facilitating instant absorption and dispersion through the skin of a user, thereby significant anti-aging effect can be resulted in a very short period of time. In particular, the significant anti-aging effect can be observed after a treatment period of 2 days and a fully restoration effect can be observed after a treatment period of 28 days.

Accordingly, in order to accomplish the above objectives, the present invention provides a nano freeze dry process of preparation for a cosmetic composition, comprising the steps of:

(a) Providing a cosmetic composition;

(b) Sterilizing the cosmetic composition and place under room temperature;

(c) Placing the cosmetic composition into a capsule container in which a content of the cosmetic composition is preferably 0.5 g; and (d) Nano freeze drying the cosmetic composition in the capsule container.

In step (d), the process of nano freeze drying the cosmetic composition in the capsule container comprises the steps of:

(d.1) freezing under a first temperature at −170 C for 2 hours;

(d.2) increasing the first temperature to a second temperature at −85° C. and allowing a process of sublimation for 8 hours at 3 Pa under vacuum condition;

(d.3) then increasing the second temperature to 35° C. at a rate of 2° C. per minute; and (d.4) vacuum drying at 0.5 Pa for 4 hours to obtain a final product and vacuum sealing the final product inside the capsule container.

The volume of the cosmetic composition remains the same before and after the above nano freeze dry process and the water content inside the final product of the cosmetic composition is less than 5%.

Preferably, in step (a), the cosmetic composition in a liquid solution having a volume of 1 kg is prepared through the steps of:

(a.1) adding 710 g of water into a breaker, heating to 60° C. and keep under 60° C.;

(a.2) stirring at 2000 rpm and sequentially adding 250 g 20% solution of *Hamamelis mollis,* 3 g of Sodium Hyaluronate (HA), 5 g of EGF, 20 g of meristematic cell materials of plant origin, 10 g of hydrolyzed collagen; 10 g of lactose and 5 g of trehalose, and then continue stirring for 60 minutes to form the cosmetic composition;

Preferably, in step (b), the cosmetic composition is sterilized by high temperature at 120° C. for 20 minutes.

The volume of the cosmetic composition in the final product is the same as the volume of the cosmetic composition before the above nano freeze dry process. The water content inside the final product of the cosmetic composition is less than 5%. The bioactivity of the final product of the cosmetic composition is at least 80% of its original form.

The final product of the cosmetic composition is then sealed under vacuum. The effective period of the final product of the cosmetic composition is 8 years. The bioactivity of the final product of the cosmetic composition is at least 80% of its original form within the effective period.

Preferably, each capsule container contains a single use amount for a user. The volume of each capsule container is arranged for containing 0.5 g of the cosmetic composition and 1 g of purified water. The user can simply tear off the aluminum cover of the capsule container and add purified water into the capsule to fill up the capsule. Then, the final product of the cosmetic composition is dissolved completely and is ready to be applied onto the skin of the user, thereby a significant anti-aging effect can be observed after a treatment period of 2 days and a fully restoration effect can be observed after a treatment period of 28 days.

DETAILED DESCRIPTION OF THE PREFERRED EMBODIMENT

The present invention is further described in details with the accompanying drawings and embodiments.

Figure 1:
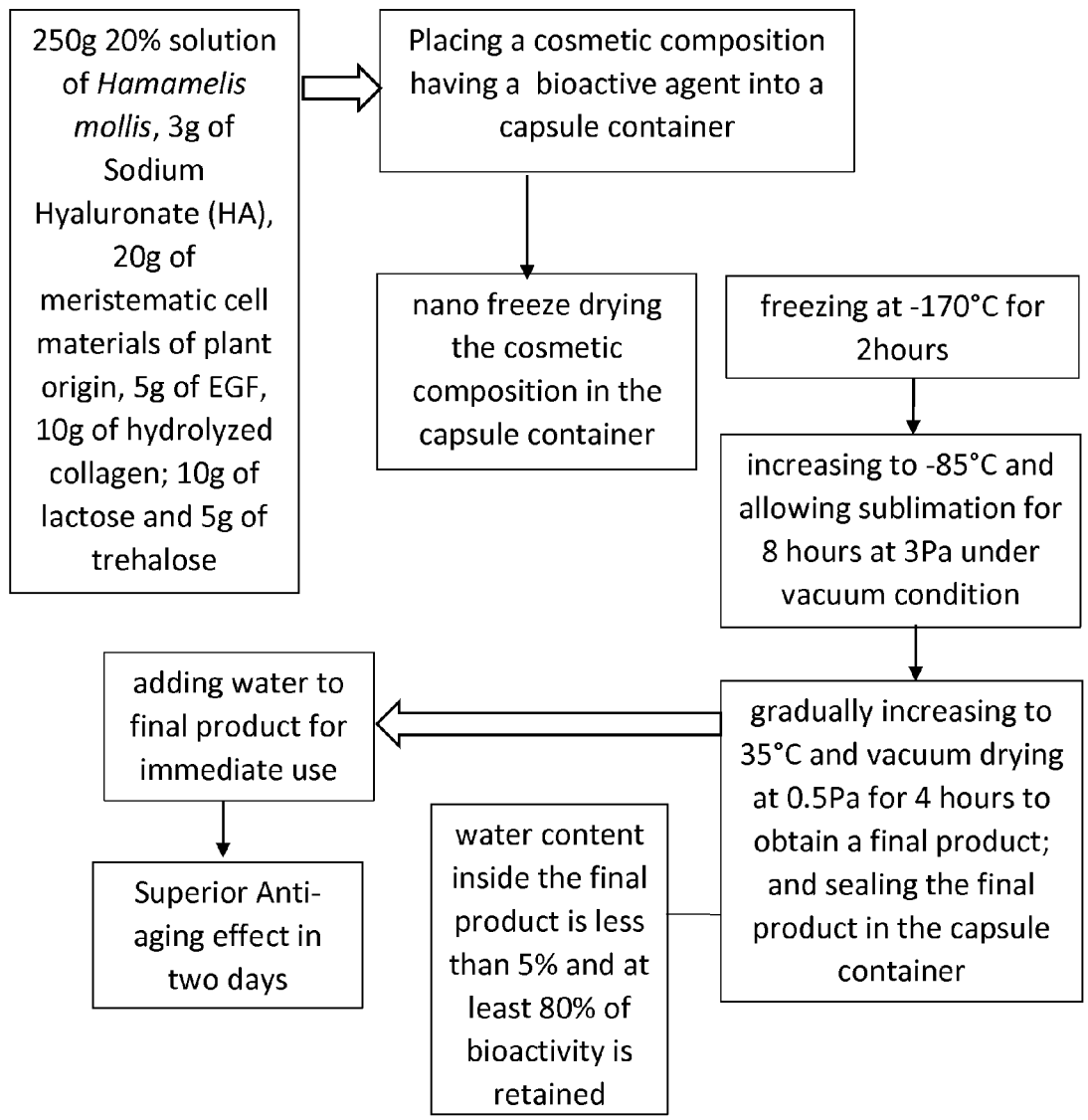
FIG. 1 illustrates a nano freeze dry process of preparation for a cosmetic composition and its method of use according to a preferred embodiment of the present invention.
Figure 2:
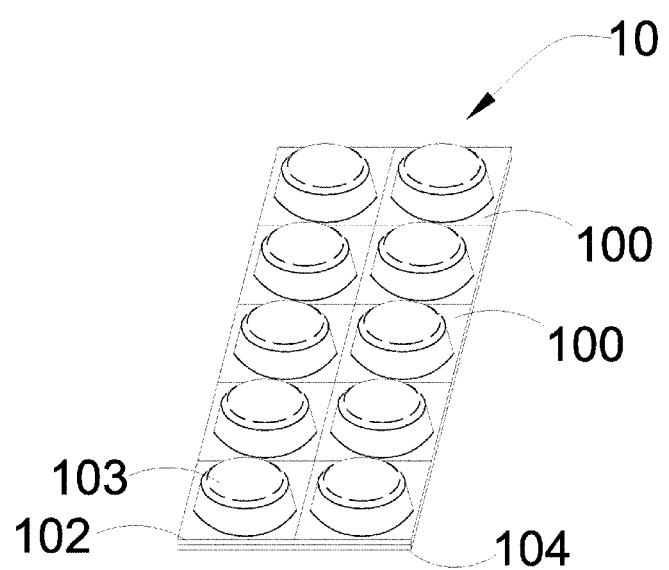
FIG. 2 is an illustration of a plurality of the capsule containers according to the above preferred embodiment of the present invention.

Referring to FIGS. 1 and 2 of the drawings, the present invention provides a nano freeze dry process of preparation for a cosmetic composition, comprising the steps of:

(a) Providing a cosmetic composition;

(b) Sterilizing the cosmetic composition and place under room temperature;

(c) Placing the cosmetic composition into a capsule container in which a content of the cosmetic composition is preferably 0.5 g; and (d) Nano freeze drying the cosmetic composition in the capsule container.

Then, after the step (d), the cosmetic composition is vacuum sealed inside the capsule container. Preferably, the process of nano freeze drying the cosmetic composition in the capsule container is an automatic process carried by a freeze drying machine.

In step (d), the process of nano freeze drying the cosmetic composition in the capsule container comprises the steps of:

(d.1) freezing under a first temperature at −170 C for 2 hours;

(d.2) increasing the first temperature to a second temperature at −85° C. and allowing a process of sublimation for 8 hours at 3 Pa under vacuum condition;

(d.3) then increasing the second temperature to 35° C. at a rate of 2° C. per minute; and (d.4) vacuum drying at 0.5 Pa for 4 hours to obtain a final product.

The volume of the cosmetic composition remains the same before and after the above nano freeze dry process and the water content inside the final product of the cosmetic composition is less than 5%.

Preferably, in step (a), a liquid solution of the cosmetic composition having a volume of 1 kg is prepared through the steps of:

(a.1) adding 710 g of water into a breaker, heating to 60° C. and keep under 60° C.;

(a.2) stirring at 2000 rpm and sequentially adding 250 g 20% solution of *Hamamelis mollis,* 3 g of Sodium Hyaluronate (HA), 20 g of meristematic cell materials of plant origin, 5 g of EFG, 10 g of hydrolyzed collagen; 10 g of lactose and 5 g of trehalose, and then continue stirring for 60 minutes to form the cosmetic composition;

Preferably, in step (b), the cosmetic composition is sterilized by high temperature at 120° C. for 20 minutes.

Embodiment 1

According to this embodiment 1 of the present invention, a nano freeze dry process of preparation of a cosmetic composition comprises the steps of:

(a) Providing a cosmetic composition which is primarily comprised of: 25% *Hamamelis mollis,* 0.3% Sodium Hyaluronate (HA), 2% meristematic cell materials of plant origin, 0.5% of EFG, 1% hydrolyzed collagen, 1% lactose and 0.5% trehalose by percentage weight;

(b) Sterilizing the cosmetic composition and place under room temperature;

(c) Placing a predetermined amount of the cosmetic composition from the step (b) into a capsule container which has a size complementary to the predetermined amount of the cosmetic composition, wherein the predetermined amount of the cosmetic composition has a weight of 0.5 g; and (d) Nano freeze drying the cosmetic composition in the capsule container.

Then, after the step (d), the cosmetic composition is vacuum sealed inside the capsule container.

According to this embodiment 1 of the present invention, in step (d), the process of nano freeze drying the cosmetic composition in the capsule container comprises the steps of:

(d.1) freezing the cosmetic composition in the capsule container at −170° C. for 2 hours;

(d.2) increasing the temperature to −85° C. and allowing a process of sublimation for 8 hours at 3 Pa under vacuum condition;

(d.3) then increasing the temperature to 35° C. at a rate of increase of 2° C. per minute; and (d.4) vacuum drying at 0.5 Pa for 4 hours to obtain a final product.

The volume of the cosmetic composition in the final product is the same as the volume of the cosmetic composition before the above nano freeze dry process. The water content inside the final product of the cosmetic composition is less than 5%. The bioactivity of the final product of the cosmetic composition is at least 80% of its original form.

The final product of the cosmetic composition is then sealed under vacuum. The effective period of the final product of the cosmetic composition is 8 years. The bioactivity of the final product of the cosmetic composition is at least 80% of its original form within the effective period.

In particular, the capsule container is made in aluminum which provides superior sealing effect, heat insulation effect and shading effect.

The final product of the cosmetic composition is in a dried powder form. Compared to an aqueous form, the reaction between different ingredients in the compositions is avoided, the stability of the cosmetic composition is highly increased, the loss of bioactivities of the ingredients of the cosmetic composition is minimized, and the toxic side products from the bioactive ingredients of the cosmetic composition is minimized to insignificant level.

Preferably, each capsule container contains a single use amount for a user. The volume of each capsule container is arranged for containing 0.5 g of the cosmetic composition and 1 g of purified water. The user can simply tear off the aluminum cover of the capsule container and add purified water into the capsule to fill up the capsule. Then, the final product of the cosmetic composition is dissolved completely and is ready to be applied onto the skin of the user.

According to this embodiment, the final product of the cosmetic composition has significant anti-aging effect. If the final product of the cosmetic composition is used twice a day, a significant anti-aging effect can be observed after a treatment period of 2 days and a fully restoration effect can be observed after a treatment period of 28 days. For examples, wrinkles is diminished after 2 days and is not visually observed after 28 days.

It is worth mentioning that since the cosmetic composition contains ingredients with high bioactivity, it is not possible to use conventional method of preparation to prepare the cosmetic composition of the present invention.

According to this embodiment 1, the final product of the cosmetic composition is tested in view of the following indicators:

TABLE 1

Health Indicators

| | Items | Standard |
|---|---|---|
| Microbial Index | Total bacteria (CFU/g) | ≤1000 |
| | Total mold and yeast (CFU/g) | ≤100 |
| Microbial Index | Fecal coliforms | Not detected |
| | Staphylococcus aureus | Not detected |
| | Pseudomonas aeruginosa | Not detected |
| Toxicity Index | Lead (mg/lg) | ≤40 |
| | Mercury (mg/lg) | ≤1 |
| | Arsenic (mg/lg) | ≤10 |
| | Methanol (mg/lg) | ≤2000 |

According to this embodiment 1, the final product of the cosmetic composition meets all the requirements of health indicators.

TABLE 2

Sensory and Physical Indicators

| | | Requirements | |
|---|---|---|---|
| | Items | Final Product (Dry Powder) | Solvent |
| Sensory Index | Appearance | Aggregated powder with fixed shape and form | Liquid |
| | Aroma | Comply with requirement | |
| Physical Index | Heat Resistance | (40 ± 1)° C., 24 h, no significant difference after recover to room temperature | |
| | Cold Resistance | (5 ± 1)° C., 24 h, no significant difference after recover to room temperature | |
| | pH | 4.0~8.5(Direct Measurement) | |
| | Relative density (20° C./20° C.) | Standard value ± 0.02 | |

According to this embodiment 1, the final product of the cosmetic composition meets all the requirements of sensory and physical indicators and the results are shown in Table 2.

It is worth mentioning that the final product of the cosmetic composition has retain high bioactivity and is resized to nano-molecular scale. Therefore, the bioactive agents in the cosmetic composition can immediately penetrate and spread into the skin instantaneously such that an unexpectedly superior anti-aging effect can be obtained in a very short period of treatment time, even for the old or middle aged users.

The superior anti-aging effect for skin is achieved through increasing membrane fluidity, increasing permeability in relation to cell activity, promoting epidermal cell growth and repair and improving immunity and resistance to diseases. The cosmetic composition, which contains highly bioactive agents and is in nano-molecular level, can effectively accelerate its compositions to enter into the skin cells, extend the effective activity time, the effective stability, reducing toxicity and irritation.

Exemplary Embodiment 2

According to this embodiment 2, all steps, materials and parameters are the same as the embodiment 1 except the followings:

In step (a), a liquid solution of the cosmetic composition having a volume of 1 kg is prepared through the steps of:

(a.1) adding 710 g of water into a breaker, heating to 60° C. and keep under 60° C.; and (a.2) stirring at 2000 rpm and sequentially adding 250 g 20% solution of *Hamamelis mollis*, 3 g of Sodium Hyaluronate (HA), 20 g of meristematic cell materials of plant origin, 5 g of EFG, 10 g of hydrolyzed collagen; 10 g of lactose and 5 g of trehalose, and then continue stirring for 60 minutes to form the cosmetic composition.

Exemplary Embodiment 3

According to this embodiment 3, all steps, materials and parameters are the same as the embodiment 1 except the followings:

The *Hamamelis mollis* in the cosmetic composition is replaced by one or more other ingredients having high bioactivity.

It is worth mentioning that the final product of cosmetic composition of the present invention, which is in powder form, can be recovered into solution form simply by adding water and then is ready for immediate use. The bioactivity of the solution has no significant difference from the powder form and is safe for use within the effective period of 8 years.

Exemplary Embodiment 4

According to this embodiment 4, all steps, materials and parameters are the same as the embodiment 1 except the followings:

All the ingredients of the cosmetic composition are derived from natural source. It is worth mentioning that the final product is natural and is safe for oral consumption.

Exemplary Embodiment 5

According to this embodiment 5, all steps, materials and parameters are the same as the embodiment 1 except the following:

The capsule container, which is made in aluminum and provides superior sealing effect, heat insulation effect and shading effect, is a type of vacuum preservation capsule made by aluminum foil.

Figure 3:
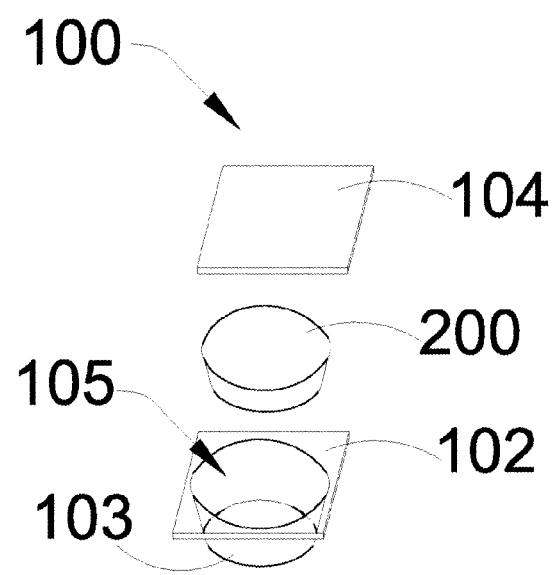
FIG. 3 is an illustration of a capsule container containing the cosmetic composition prepared by the nano freeze dry process of preparation according to the above preferred embodiment of the present invention.

Referring to FIG. 2 of the drawings, a plurality of capsule containers 10 containing the cosmetic composition 200 of which each capsule container 100 are divided by easy cutting lines are illustrated. In particular, referring to FIGS. 2 and 3 of the drawings, each capsule container 100 comprises a main body 102, a bottom body 103 defining a receiving cavity 105 arranged for receiving the cosmetic composition 200, and a sealing cover 100. It is worth mentioning that the capsule container 100 is made in aluminum foil and the cosmetic composition 200 is vacuum sealed inside the receiving cavity 105 of the capsule container 10. Preferably, a volume of the capsule container is arranged for receiving a single use quantity. A user can simply remove the sealing cover 100 and add water into the receiving cavity 105, then the cosmetic composition 200 will become a cream or lotion which can be used immediately.

According to the cosmetic composition of the present invention, the cosmetic composition in the capsule container is frozen and cut into nano-molecular scale through the ultra-low temperature state at its critical point. Since the particle size of the cosmetic composition is re-sized from macromolecular to nanomolecular level, the active ingredients can be absorbed by the skin cell instantaneously. As a result, the cosmetic composition of the present invention is capable of providing superior moisturizing, replenishing and anti-aging effect.

In particular, the cosmetic composition in nano-molecular size can be entered into the skin cell as a whole or can be divided into smaller pieces by the skin cells.

The cosmetic composition in the capsule container according to the present invention has the following characteristics:

(1) Easy and convenience to use in a precise manner: A user can simply add water into the capsule container and the cosmetic composition will dissolve and become a cream, which is suitable for use in facial application.

(2) Total Green Cosmetic Composition: The cosmetic composition has no added chemicals, preservatives, emulsifiers, artificial colors or flavors.

(3) Convenience to carry: Each individual capsule container contains one single use dosage, which is approximately the size of a penny. There is no need to carry cosmetic bottle and there is no concerns about spillage or evaporation problems.

(4) Superior anti-aging effect: since all the cosmetic compositions are re-sized to nano molecules through the nano freeze dry process of preparation of the present invention, the cosmetic compositions can enter and absorb into the skin cells easily. Compared to the conventional cream or lotion for skin use, since the active ingredients are encapsulated by macromolecular oil particles, the penetration and absorption of the active ingredients are seriously affected. This problem is particularly significant for macromolecules such as SOD which has a molecular weight of 3000 or above. As a result, it is very difficult for the active ingredients to enter into the skin cell through the stratum corneum. As the cosmetic composition of the present invention is in nano-molecular level without any oil particle for encapsulation, the anti-aging effect, the moisturizing effect and the replenishing effect of the cosmetic composition of the present invention can be increased by hundreds of times when comparing to the convention cosmetic cream or lotion.

(5) High sustained-releasing ability: the cosmetic composition can stay inside and outside the skin cells such that the bioactive agents can be permeated slowly such that an effective activity time can be increased.

(6) High stability: Compared to conventional compositions with SOD, Vitamin E, Vitamin C or EGF agents, the composition is very unstable and is easily affected by enzyme and ultraviolet light. The cosmetic compositions in the capsule container, which contains very low level of water and is protected by the capsule container, has dramatically increased its effective period through avoiding the activity of enzyme and ultraviolet light, while is capable of turning into a cream or lotion form for application with a simple step of adding water.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A nano freeze dry process of preparation for a cosmetic composition having a bioactive agent for providing an anti-aging effect on a skin, comprising the steps of:
   (a) placing a cosmetic composition having a bioactive agent into a capsule container; and
   (b) nano freeze drying the cosmetic composition in the capsule container;
   wherein in the step (b), comprises the steps of:
   (b.1) freezing the cosmetic composition in the capsule container at −170° C. for 2 hours;
   (b.2) increasing the temperature to −85° C. and allowing a process of sublimation for 8 hours at 3 Pa under vacuum condition; and
   (b.3) then increasing the temperature to 35° C. at a rate of increase of 2° C. per minute; and
   (d.4) vacuum drying at 0.5 Pa for 4 hours to obtain a final product of the cosmetic composition and vacuum sealing the capsule container, wherein a volume of the final product of the cosmetic composition is the same as a volume of the cosmetic composition before the step (b), a water content inside the final product of the cosmetic composition is less than 5%, and at least 80% of bioactivity of the cosmetic composition is retained in the final product of the cosmetic composition.

2. The nano freeze dry process of preparation according to claim 1, wherein in the step (a), a weight of the cosmetic composition is 0.5 g, a volume of the capsule container is arranged for containing 0.5 g of the cosmetic composition and 1 g of water.

3. The nano freeze dry process of preparation according to claim 1, wherein in the step (a), the cosmetic composition is a liquid solution having a volume of 1 kg prepared by the steps of:
   (a.1) adding 697 g of water into a breaker, heating to 60° C. and keep under 60° C.; and
   (a.2) stirring at 2000 rpm and sequentially adding 250 g 20% solution of *Hamamelis mollis*, 3 g of Sodium Hyaluronate (HA), 20 g of meristematic cell materials of plant origin, 5 g of EGF, 10 g of hydrolyzed collagen; 10 g of lactose and 5 g of trehalose, and then continue stirring for 60 minutes to form the cosmetic composition,
   wherein the anti-aging effect on the skin is observed within a two-day treatment.

4. The nano freeze dry process of preparation according to claim 1, wherein in the step (a), the cosmetic composition is a liquid solution prepared by the steps of:
   (a.1) adding 69.70% of water by percentage weight into a breaker, heating to 60° C. and keep under 60° C.; and
   (a.2) stirring at 2000 rpm and sequentially adding 25% of *Hamamelis mollis* by percentage weight, 0.3% of Sodium Hyaluronate (HA) by percentage weight, 2% of meristematic cell materials of plant origin by percentage weight, 1% of hydrolyzed collagen by percentage weight; 0.5% of EGF by percentage weight, 1% of lactose by percentage weight and 0.5% of trehalose by percentage weight, and then continue stirring for 60 minutes to form the cosmetic composition,
   wherein the anti-aging effect on the skin is observed within a two-day treatment.

5. A nano freeze dry process of preparation for a cosmetic composition having a bioactive agent for providing an anti-aging effect on a skin, comprising the steps of:
   (a) placing a cosmetic composition having a bioactive agent into a capsule container; and
   (b) nano freeze drying the cosmetic composition in the capsule container;
   wherein in the step (a), a plurality of capsule containers are provided such that the nano freeze dry process is capable of carrying out with the plurality of capsule containers simultaneously;
   wherein in the step (b), comprises the steps of:
   (b.1) freezing the cosmetic composition in the capsule container at −170° C. for 2 hours;
   (b.2) increasing the temperature to −85° C. and allowing a process of sublimation for 8 hours at 3 Pa under vacuum condition; and
   (b.3) then increasing the temperature to 35° C. at a rate of increase of 2° C. per minute; and (d.4) vacuum drying at 0.5 Pa for 4 hours to obtain a final product of the cosmetic composition,
   wherein a volume of the final product of the cosmetic composition is the same as a volume of the cosmetic composition before the step (b), a water content inside the final product of the cosmetic composition is less than 5%, and at least 80% of bioactivity of the cosmetic composition is retained in the final product of the cosmetic composition.

6. The nano freeze dry process of preparation according to claim 5, wherein in the step (a), a weight of the cosmetic composition is 0.5 g, a volume of the capsule container is arranged for containing 0.5 g of the cosmetic composition and 1 g of water.

7. The nano freeze dry process of preparation according to claim 6, wherein in the step (a), the cosmetic composition is a liquid solution having a volume of 1 kg prepared by the steps of:
   (a.1) adding 697 g of water into a breaker, heating to 60° C. and keep under 60° C.; and
   (a.2) stirring at 2000 rpm and sequentially adding 250 g 20% solution of *Hamamelis mollis*, 3 g of Sodium Hyaluronate (HA), 20 g of meristematic cell materials of plant origin, 10 g of hydrolyzed collagen; 5 g of EGF, 10 g of lactose and 5 g of trehalose, and then continue stirring for 60 minutes to form the cosmetic composition,
   wherein the anti-aging effect on the skin is observed within a two-day treatment.

8. The nano freeze dry process of preparation according to claim 6, wherein in the step (a), the cosmetic composition is a liquid solution prepared by the steps of:
   (a.1) adding 69.7% of water by percentage weight into a breaker, heating to 60° C. and keep under 60° C.; and
   (a.2) stirring at 2000 rpm and sequentially adding 25% of *Hamamelis mollis* by percentage weight, 0.3% of Sodium Hyaluronate (HA) by percentage weight, 2% of meristematic cell materials of plant origin by percentage weight, 1% of hydrolyzed collagen by percentage weight; 5% of EGF by percentage weight, 1% of lactose by percentage weight and 0.5% of trehalose by percentage weight, and then continue stirring for 60 minutes to form the cosmetic composition,
   wherein the anti-aging effect on the skin is observed within a two-day treatment.

\* \* \* \* \*